United States Patent [19]

Baehr

[11] 4,084,612
[45] Apr. 18, 1978

[54] FLOW COMPENSATING PRESSURE REGULATOR

[75] Inventor: Edward F. Baehr, Berea, Ohio

[73] Assignee: The United States of America as represented by the Administrator of the National Aeronautics and Space Administration, Washington, D.C.

[21] Appl. No.: 779,428

[22] Filed: Mar. 21, 1977

[51] Int. Cl.² ............................................. F16K 17/34
[52] U.S. Cl. .................. 137/484.2; 137/501; 137/505.16
[58] Field of Search ............... 137/484.2, 484.4, 484.6, 137/484.8, 505.14, 505.16, 501

[56] References Cited

U.S. PATENT DOCUMENTS

| 2,182,873 | 12/1939 | King | 137/484.2 |
| 3,433,254 | 3/1969 | Frascati | 137/505.16 |

*Primary Examiner*—Harold W. Weakley
*Attorney, Agent, or Firm*—N. T. Musial; J. R. Manning; J. A. Mackin

[57] ABSTRACT

Apparatus for regulating pressure of treatment fluid being supplied to a human or animal eye during ophthalmic procedures such as cataract surgery is disclosed.

Flow sensing and pressure regulating diaphragms are provided in a body to modulate a flow control valve. The pressure regulating diaphragm is connected to the flow control valve to urge the valve to an open position due to pressure being applied to the diaphragm by bias means such as a spring. The flow sensing diaphragm is mechanically connected to the flow control valve and urges it to an opened position because of the differential pressure on the diaphragm generated by a flow of incoming treatment fluid through an orifice in the diaphragm. A bypass connection with a variable restriction is connected in parallel relationship to the orifice to provide for adjusting the sensitivity of the flow sensing diaphragm.

A multiple lever linkage system is utilized between the center of the second diaphragm and the flow control valve to multiply the force applied to the valve by the other diaphragm and reverse the direction of the force.

A vertically extending tube communicates with the upper side of the pressure regulating diaphragm which also communicates with an auxiliary outlet port.

17 Claims, 1 Drawing Figure

U.S. Patent      April 18, 1978      4,084,612
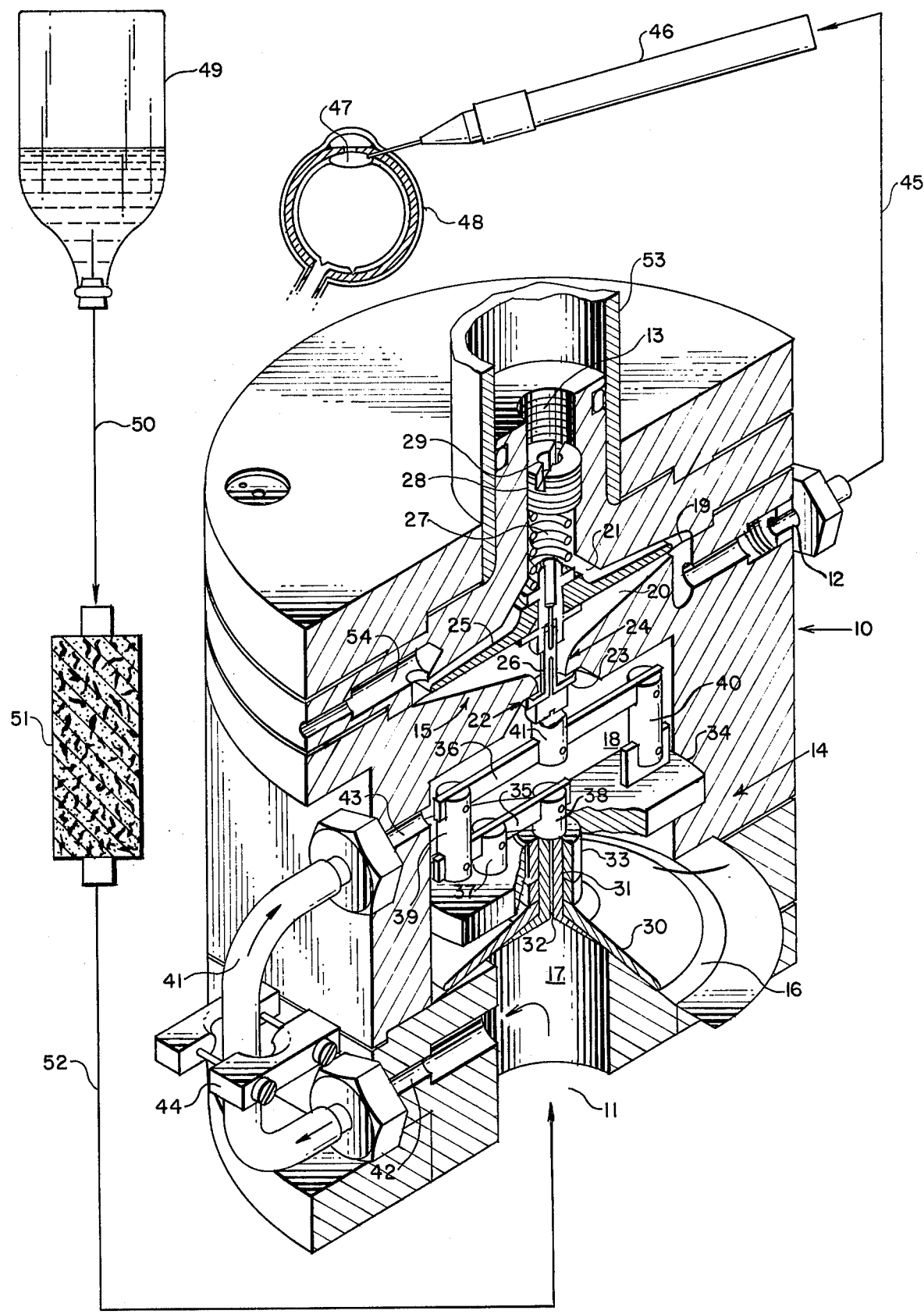

FLOW COMPENSATING PRESSURE REGULATOR

ORIGIN OF THE INVENTION

This invention described herein was made by an employee of the United States Government and may be manufactured or used by or for the Government without the payment of any royalties thereon or therefor.

BACKGROUND OF THE INVENTION

In many ophthalmic procedures, as for example cataract surgery, fluid under pressure is often supplied to the operative site to maintain a desired pressure in the eye. In recent years there have been a number of advances in cataract surgery techniques wherein instruments are inserted through the cornea of an eye to mascerate the lens material. Treatment fluid is supplied to the operative site through the surgical instrument and mascerated material and treatment fluid are withdrawn either through the surgical instrument or by an ancillary conduit.

In some cases the pressure of the treatment fluid delivered to the operative site is controlled simply by elevating or lowering a reservoir containing the treatment fluid. Obviously, this procedure cannot compensate for variations in pressure caused by changes in the rate of fluid flow or other conditions which vary the pressure.

In one cataract surgical procedure a computer is used to control pressure and also to monitor fluid flow rate so that surges will not cause a pressure rise great enough to damage the eye. Such apparatus is both complex and expensive.

Pressure regulators of the type utilizing a spring biased diaphragm are well-known. Such regulators are generally restricted to a limited range of flow rate and rapidly lose their regulating effect outside of that range.

OBJECTS AND SUMMARY OF THE INVENTION

It is an object of the invention to provide a new and novel apparatus for regulating the pressure of a fluid at a site away from a source of pressurized fluid.

It is another object of the invention to provide a pressure regulator which maintains an accurate pressure regulation over a relatively wide range of change in the flow rate of fluid through the regulator.

Another object of the invention is to provide a pressure regulator which can be adjusted to alter the permissible variation in pressure resulting from any given change in fluid flow rate.

Still another object of the invention is to provide a pressure regulator which is compact and relatively inexpensive.

Yet another object of the invention is to provide a pressure regulator which utilizes the weight of a liquid to modify a pressure regulating characteristics of the regulator for use in certain types of ophthalmic procedures wherein pressure in the eye can be reduced at a predetermined rate.

BRIEF DESCRIPTION OF THE DRAWING

The single FIGURE shows an oblique longitudinal sectional view of a pressure regulator embodying the invention together with schematically illustrated ophthalmic surgical equipment.

DESCRIPTION OF A PREFERRED EMBODIMENT

Referring now to the single FIGURE, there is shown a pressure regulator comprising a body 10 having therein an inlet port 11, an outlet port 12, an ambient port 13, a first chamber 14 and a second chamber 15. A flow sensing diaphragm 16 divides the first chamber into an inlet subchamber 17 and a flow control subchamber 18. Similarly, a diaphragm 19 divides chamber 15 into a regulated outlet subchamber 20 and an ambient pressure subchamber 21. A valve means 22 which serves as a flow control valve means is disposed between chamber 14 and chamber 15 and may comprise a poppet member 23 which seats against the rim of an orifice 24.

Diaphragm 19 has attached thereto a backing plate 25 which engages a stem 26 of poppet 23. Consequently, any movement of the diaphragm 19 toward the regulated outlet subchamber 20 will move poppet 23 off its seat to permit fluid flow through the orifice 24. To this end, a coil spring 27 is disposed between the backing plate 25 of diaphragm 19 and a threaded plug 28 having an orifice 29 therein. The threaded plug 28 may be rotated to increase or decrease the pressure exerted on diaphragm 19 by the spring 27 which serves as a bias means.

The flow sensing diaphragm 16 is supported on a backing plate 30 having an upwardly extending stem 31 with a sensing orifice 32. A spacer 33 is disposed around stem 31 and with a pivot nut 38 is free to move vertically through a pivot support plate 34 to engage a multiple linkage system as will now be described.

The multiple lever linkage system is interposed between the stem 31 of diaphragm 16 and the poppet 23 of valve means 22 and serves to multiply the pressure of diaphragm 16 resulting from fluid flow through the orifice 32. The multiple lever linkage comprises a lever arm 35 and a lever arm 36.

Lever arm 35 pivots about a fixed pivot 37 intermediate its ends and mounted on pivot support plate 34. One end of lever 35 is pivotally connected by pivot nut 38 to stem 31 of diaphragm 16 while the other end is pivotally connected by a link 39 to one end of lever arm 36. The other end of lever arm 36 is attached to a fixed pivot point provided by the pivot link 40 mounted on pivot support plate 34. A point intermediate the ends of lever arm 36 is pivotally connected by link 41 to the poppet 23.

With this arrangement, it will be seen that upward movement of diaphragm 16 and stem 31 produces downward movement of pivot 41. The poppet 23 is consequently pulled off its seat opening valve 22.

The use of the multiple lever linkage system multiplies the effect of sensing diaphragm 16 on poppet 23. This advantageously allows diaphragms 16 and 19 to be approximately the same size. However, the multiplication effect can be achieved by making diaphragm 16 much larger in area than diaphragm 19 as, for example, two to fifteen times as large.

As will be seen from the figure, the multiplication factor of the multiple lever of linkage is determined by the positioning of fixed pivot 37 and intermediate pivot 41. The positioning of fixed pivot 37 alone is sufficient to give a wide range of multiplication factors.

The pressure on the diaphragm 16 due to fluid flow through orifice 32 together with the multiplication factor of the multiple lever system and the bias exerted by spring 27 on poppet 23 by way of diaphragm 18 are all factors in the determination of the pressure which appears at the outlet port 12. The sensitivity of the pressure regulator to changes in the rate of fluid flow is closely related to the pressure drop caused by fluid flow through orifice 32. To the end that the sensitivity may be adjusted, a conduit 41 is connected between a bypass outlet port 42 communicating with inlet subchamber 17 and a bypass inlet port 43 communicating with regulating subchamber 18. The sensitivity is adjusted by means of a pinch valve 44 disposed around the bypass conduit 41. It will be obvious that any suitable valve may be inserted in the bypass conduit 41.

The outlet port 12 of pressure regulator 10 is connected through a conduit 45 to the ophthalmic lens mascerating tool 46 from which it flows to the operative site such as lens 47 of eye 48. The fluid is obtained from a treatment fluid reservoir 49 from which it flows through a passageway 50, a filter 51 and a passageway 52 to the inlet port 11 of the pressure regulator 10. The pressure of the fluid at inlet port 11 is determined by the height of reservoir 49 and should be substantially greater than the desired regulated pressure at outlet port 12.

In certain types of operations where it may be desirable to gradually reduce the pressure in an eye, a vertical tube 53 may extend vertically upward from ambient port 13, and an auxiliary port 54 in communication with the ambient subchamber 21 may be provided. The vertical tube 53 may be filled with a liquid, the weight of which is impressed through plug 28 onto diaphragm 19 to alter the pressure regulating characteristics of the regulator 10. A bleed line, valve or conduit (not shown) may be attached to auxiliary port 54 to gradually reduce the liquid level in the tube 53.

In operation, treatment fluid from reservoir 49 enters the inlet port 11 and then flows through the orifice 32 into subchamber 18. The pressure drop developed across orifice 32 causes the diaphragm 16 and stem 31 to move upwardly as viewed in the drawing. This causes the pivot 41 to exert a downward force on poppet 23 tending to open the flow control valve 22. The downward force on poppet 23 is added to the downward force already applied thereto by spring 27 through backing plate 25 and diaphragm 19. The fluid passing through orifice 32 then passes through the flow control valve 22 into the regulating subchamber 20 and outlet port 12 to the ophthalmic instrument 46. From the foregoing explanation, it will be seen that as additional fluid is required at the operative site in lens 47, the pressure drop across orifice 32 will increase adding additional downward force through the poppet 23. This allows additional fluid to flow through the valve 22 while at the same time reducing the pressure drop at that point so that the desired pressure may be maintained at the operative site.

As discussed previously, some of the fluids entering inlet port 11 may be diverted through the bypass outlet 42, the conduit 41 and the bypass inlet 43. This parallel flow of treatment fluid reduces the pressure drop across the orifice 32 to alter those pressure regulating characteristics of the pressure regulator which are responsive to changes in the fluid flow rate. This sensitivity is adjustable by means of the pinch valve 44 disposed around the conduit 41.

Under conditions in which no fluid flow is being delivered to the operative site in eye 48 there is, of course, no pressure drop across orifice 32. Under these conditions, the pressure at outlet 12 is regulated by the pressure of spring 27 on the backing plate 25 of diaphragm 19. This pressure is adjustable by means of the threaded plug 28.

It will be understood that changes and alterations may be made to the above-described pressure regulator without departing from the spirit and scope of the invention as set forth in the claims appended hereto.

What is claimed is:

1. A pressure regulator comprising:
    a body having an inlet port, an oulet port, an ambient port, and including a first chamber and a second chamber;
    a flow sensing diaphragm disposed in said first chamber and forming an inlet subchamber and a flow control subchamber, said diaphragm having therein a signal generating orifice, said inlet subchamber being in communication with said inlet port;
    a pressure regulating diaphragm disposed in said second chamber and forming a regulated outlet subchamber and an ambient pressure subchamber, said regulated outlet subchamber being in communication with said outlet port;
    flow control valve means disposed between said flow control subchamber and said regulated outlet subchamber;
    means operatively connecting said pressure regulation diaphragm to said valve means;
    bias means urging said pressure regulating diaphragm into said regulated outlet subchamber and thereby urging said valve means to an open position; and
    means operatively connecting said flow sensing diaphragm to said valve means, said flow sensing diaphragm urging said valve means to an open position due to pressure drop across said orifice when fluid flows therethrough.

2. The pressure regulator of claim 1 and including bypass means for directing fluid from said inlet subchamber to said flow control chamber to modify the pressure drop across said orifice.

3. The pressure regulator of claim 2 wherein said bypass means includes a variable flow restrictor.

4. The pressure regulator of claim 1 wherein said flow sensing diaphragm is substantially larger in area than said pressure regulating diaphragm.

5. The pressure regulator of claim 4 wherein said flow sensing diaphragm is at least two times greater in area than said pressure regulating diaphragm.

6. The pressure regulator of claim 1 wherein said bias means is a coil spring.

7. The pressure regulator of claim 1 wherein said means operatively connecting said flow sensing diaphragm to said valve means is a multiple lever linkage.

8. The pressure regulator of claim 7 wherein said multiple lever linkage multiplies the force applied to the valve means by at least a factor of two times the force at the center of said flow sensing diaphragm.

9. The pressure regulator of claim 7 wherein said multiple lever linkage comprises first and second lever arms, said first lever arm being shorter than said second lever arm and pivoting on a fixed pivot intermediate its ends, one end being pivotally connected to the center of said flow sensing diaphragm and the other end being pivotally connected to one end of said second lever arm, the other end of said second lever arm being pivotally connected to a fixed pivot, a point intermediate the ends of said second lever arm being pivotally connected to said flow control valve means.

10. The pressure regulator of claim 9 wherein said pivot points are positioned such that the force exerted on said valve means is at least twice as great as that applied to said one end of said first lever arm by said flow sensing diaphragm.

11. The pressure regulator of claim 9 wherein said pivot points are positioned such that the force exerted on said valve means is about five times as great as that applied to said one end of said first lever arm by said flow sensing diaphragm.

12. The pressure regulator of claim 1 wherein the centers of said flow sensing and pressure regulating diaphragms lie on a common axis perpendicular to said diaphragms.

13. The pressure regulator of claim 1 and further including an auxiliary outlet port in communication with said ambient chamber and a tube extending generally vertically from said ambient port.

14. The pressure regulator of claim 1 wherein said orifice is at the center of said flow sensing diaphragm.

15. In a pressure regulator of the type comprising a body including a chamber and a biased diaphragm with a fluid inlet and a fluid outlet communicating with one side of the diaphragm, and a flow valve controlled by the diaphragm, the improvement comprising a vertically extending fluid tube communicating with the other side of the diaphragm and with an auxiliary port in the body, and bleed means communicating with the auxiliary port whereby the weight of a fluid disposed in said fluid tube adds to the normal bias on the diaphragm and whereby the bias may be reduced to normal as the height of fluid in said tube is reduced by the bleed means.

16. The regulator of claim 1 wherein said bleed means is a length of tubing.

17. The regulator of claim 16 wherein said tubing has an inside diameter of 0.031 inch.

* * * * *